United States Patent [19]
Szabo et al.

[11] Patent Number: 6,136,289
[45] Date of Patent: Oct. 24, 2000

[54] PREPARATION PROCESS FOR FERRIERRITE ZEOLITE AND ITS USES AS AN ISOMERIZATION CATALYST OF LINEAR OLEFIN IN ISOOLEFIN OR AS A HYDROCRACKING AND HYDROISOMERIZATION PARAFFIN CATALYST

[75] Inventors: Georges Szabo, Montivilliers; Paul Meriaudeau, Pont d'Ain; Anh Tuan Vu, Villeurbanne; Sebastien Decker, Le Havre, all of France

[73] Assignee: Total Raffinage Distribution S.A., Puteaux, France

[21] Appl. No.: 09/124,920

[22] Filed: Jul. 30, 1998

[30] Foreign Application Priority Data

Jul. 31, 1997 [FR] France ................... 97 09768

[51] Int. Cl.[7] .................................... C01B 39/44
[52] U.S. Cl. ................... 423/700; 423/710; 423/711; 423/DIG. 23
[58] Field of Search .................. 423/700, 710, 423/711, 713, DIG. 23

[56] References Cited

U.S. PATENT DOCUMENTS

| | | |
|---|---|---|
| 3,933,974 | 1/1976 | Winquist . |
| 3,966,883 | 6/1976 | Vaughan et al. .................. 423/712 |
| 3,992,466 | 11/1976 | Plank et al. . |
| 4,017,590 | 4/1977 | Cormier et al. .............. 423/DIG. 23 |
| 4,205,053 | 5/1980 | Rollmann et al. .................. 423/705 |
| 4,650,654 | 3/1987 | Arika et al. . |
| 4,687,654 | 8/1987 | Taramasso et al. .......... 423/DIG. 23 |
| 4,853,203 | 8/1989 | Guth et al. ................... 423/DIG. 23 |
| 4,967,020 | 10/1990 | Marler et al. ..................... 568/896 |
| 5,516,959 | 5/1996 | Rahmim et al. ................... 585/671 |

FOREIGN PATENT DOCUMENTS 523 838   1/1993   European Pat. Off. .

*Primary Examiner*—Mark L. Bell
*Assistant Examiner*—David Sample
*Attorney, Agent, or Firm*—Sughrue, Mion, Zinn, Macpeak & Seas, PLLC

[57] ABSTRACT

A process of preparing a ferrierite-type zeolite, with high crystallinity rate and having a anhydrous stage composition expressed by the formula $M_x(AlO_2)_x(SiO_2)_y$, M being a cation of an alkaline metal such as Na or K, or a mix of both. The process contains a gel-producing step, by addition of boric acid to an aqueous aluminum-sulfate solution mixed with a aqueous solution containing oxides of Na and/or K and of Si, without the use of a structural agent. The invention also pertains to any zeolite obtained by this process, and its uses.

11 Claims, 1 Drawing Sheet

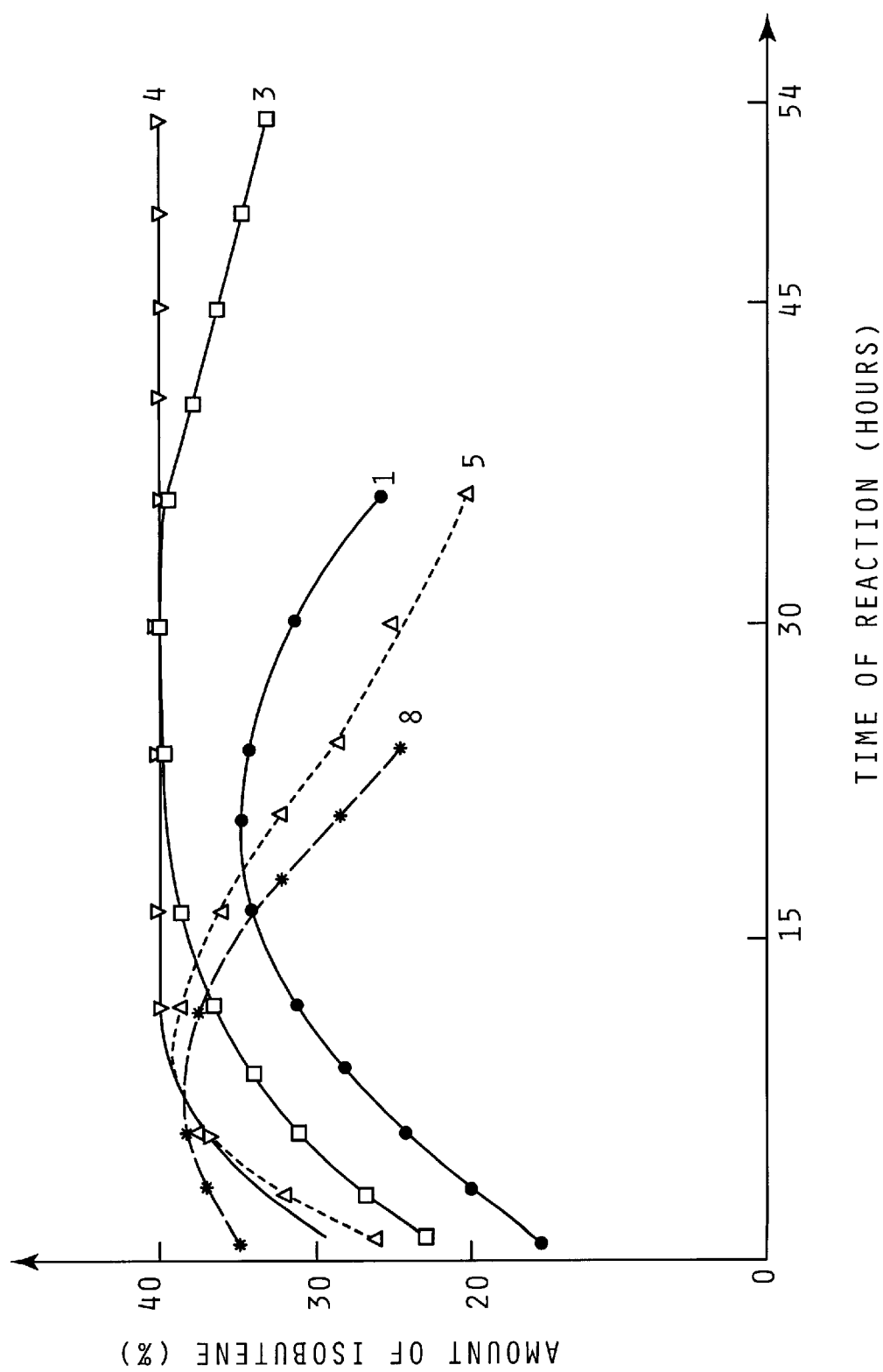

PREPARATION PROCESS FOR FERRIERRITE ZEOLITE AND ITS USES AS AN ISOMERIZATION CATALYST OF LINEAR OLEFIN IN ISOOLEFIN OR AS A HYDROCRACKING AND HYDROISOMERIZATION PARAFFIN CATALYST

BACKGROUND OF THE INVENTION

This invention relates to a preparation process of crystallographically pure ferrierite-structure (FER) synthetic zeolite with crystal size homogeneously dispersed without the use of structural agent, of its use as an acidic catalyst, particularly for the frame-structural isomerization of linear olefins such as butenes of pentenes, and as a hydrocracking and hydroisomerization catalyst of linear, or barely ramified, long-chained paraffins, notably those that result from the Fisher-Tropsch reaction from the synthesis gas ($CO+H_2$).

It is known, in the field, that the materials called zeolites, may they be natural or synthetics, possess catalytic properties for the conversion of diverse types of hydrocarbons. Typically, these materials are porous crystalline aluminosilicates whose crystalline structure is well defined, and contain a large number of very small canals or pores of a uniform size, adapted for the absorption of specific-size molecules. Ferrierite zeolite is among these natural aluminosilicate zeolites.

A great variety of ways to obtain synthetic zeolites have been previously described, in particular zeolite A (U.S. Pat. No. 2,882,243), zeolite Y (U.S. Pat. No. 3,130,007), and the so-called zeolite ZSM-5 (U.S. Pat. No. 3,702,886).

Likewise, U.S. Pat. No. 4,016,245 describes the synthesis of a alumino-silicate crystalline zeolite, named ZSM-5, that possess a crystallographic structure very similar to that of the ferrierite and that can be used as a catalyst for the conversion of hydrocarbon conversion. Nevertheless, this synthesis always involves an organic-nitrogen compound such as ethylenediamine or pyrrolidine, which behaves like a structuring agent, orienting the synthesis towards a predetermined structure. This zeolite has a orthohombic network made of two series of unidimensional canals that cross perpendicularly, one series being composed of canals of 10 "T atoms" (tetrahedric Si and AJ atoms) of slightly elliptic section (4.2×5.4 Å), and the other of canals of 8 "T atoms" (3.5×4.8 Å).

Other patents show a process of fabrication of this material which uses diverse structuring agents such as alkylpyridines (U.S. Pat. No. 4,251,499) or alkylpyperidines (U.S. Pat. No. 4,795,623) or other agents.

It is known, by the demand for Patent EP 0523 838 (Lyondell), that it is possible to use a process of skeletal isomerization of linear olefines and isoolefines, such as butene-1 or pentene-1, a catalyst of zeolite type having a structure and a dimension of pores adapted especially to reduce parasitic reactions and cokage. That document describes many types of zeolites, ferrierites among them, but does not mention the process of their manufacture.

A recent study by Wen Quing Xu et al., published in J. Phys. Chem. 1995 Vol. 99, 9443–9451, which compared the structures of different zeolites ZSM-5 of ferrierite type, synthesized respectively with a structuring agent (pyrrolidine) and without this agent, having a Si/Al ratio between 5.7 and 9.2, shows that the first category presents particles whose size displays a uniform distribution whereas the size of the crystallines in the second category is very heterogeneous, varying from a few $\mu$m to 100 $\mu$m. Furthermore, the zeolites of the first category present a higher crystallinity and contains less mesoporosites than the zeolites obtained without structuring agent. The result is an augmentation of the selectivity in skeletal isomerization of linear butene in isobutene for the zeolites synthesized with structuring agent.

This study further explains that the successful synthesis of ferrierite-type ZSM-35 zeolite, without using organic structuring agents, requires the presence of precursory gels that have a narrow Si/Al margin (roughly equal to 9) and agitating during the autoclave treatment.

SUMMARY OF THE INVENTION

The goal of this invention is thus to propose a process through which, without the use of structuring agents, one can obtain ferrierite-type zeolite that will be well crystallized, with small size and evenly distributed crystals, and that possess good catalytic properties in acid reactions such as the isomerization of butenes in isobutene or of pentenes in isopentene, and as a hydrocracking and hydroisomerization catalyst of long-chained and of linear, or barely ramified, long-chained paraffins, notably those that result from the Fisher-Tropsch reaction from the synthesis gas ($CO+H_2$).

In particular, this invention is about the process of preparation of a ferrierite-type zeolite, with high crystallinity rate and having a anhydrous stage composition expressed by the formula $M_x(AlO_2)_x(SiO_2)_y$, M being a cation of an alkaline metal such as Na or K, or a mix of both, characterized in that there is a step to obtain a gel, by the addition of boric acid to an aqueous solution of aluminum sulfate and mixed with an aqueous solution containing Na and/or K and Si oxides, without the use of structuring agent.

Preferably, the mix of the solutions is performed under agitation, with acidification reaching pH 8.

According to a preferred technique, the gel obtained is washed with distilled water.

Advantageously, a solution containing alkaline metals hydroxides is added under agitation to the mix of solutions.

The gel obtained can undergo an aging period, followed by a crystallization period in autoclave, under agitation and heat, for several hours, and the product obtained can be washed with water and heat-dried.

According to a process particular to this invention, the steps of gel manufacture and the adding of the alkaline metals hydroxides are performed at a temperature ranging between 40° and 90° C., and the aging period is performed at a temperature ranging between 25° and 80°, for a duration ranging from 6 to 72 hours.

According to a variation in the process, the crystallization period is followed by a calcination, of an impregnation with a platinum salt solution, then an evaporation, a drying, then by another calcination.

An important characteristic of the invention's process resides in the fact that the boron atoms do not stay in a crystalline structure, but end up, at the conclusion of the autoclave period, in the liquid phase.

The aging step also has an important influence on the crystallinity of the obtained zeolite, as well as the conditions of the treatment in the autoclave, notably its duration (hydrothermal synthesis).

An important advantage of the preparation process of the zeolite according to the invention resides in the suppression of the usual 500° calcination step, when an organic structuring agent is used.

The ferrierite-structured zeolite obtained by the preceding process constitutes another part of this invention.

This zeolite, as indicated above, has a formula of $M_x(AlO_2)_x(SiO_2)_y$, and the y/x ratio is usually between 8 and 12.

The average size of the zeolite crystals obtained by the process described in the invention ranges from 0.1 and 1 $\mu$m.

The invention also concerns the use of the zeolite obtained by the process described above as skeletal isomerization catalyst of the olefins, in particular of butenes in isobutenes and of pentenes in isopentenes.

Preferably, the temperature of the isomerization reaction ranges from 250 and 500°. The weight of olefins by weight of the catalyst and by hour (pph) ranges from 0.5 and 200 h−1, and the partial pressure of olefins ranges from 10 and 400 kPa. Preferably, the olefine is diluted in an inert gas such as ozone or hydrogen, granting a better stability to the catalyst.

The invention also has for goal the use of the zeolite obtained by the process described in the invention as a hydrocracking and hydroisomerization catalyst of long-chained and of linear, or barely ramified, long-chained paraffins, that can notably be obtained by the conversion of the synthesis gas ($CO+H_2$) according to the Fisher-Tropsch reaction. Actually, the hydrocracking and/or the hydroisomerization of the products resulting from the Fisher-Tropsch reaction is necessary to obtain either the "great" products (naphtha, medium distillates) of the specialties (paraffins, high-range lubricants). The reaction temperature preferably ranges from 100° C. and 350° C., the weight of the paraffin by weight of the catalyst and by hour (pph) ranges from 0.1 and 10 $h^{-1}$ and the pressure ranges from 0.01 and 10 Mpa.

BRIEF DESCRIPTION OF THE DRAWING

FIG. 1 shows the yield of isobutene (in percentage) as a function of reaction time (in hours) for the zeolites of Examples 1, 3 to 5 and 8.

DETAILED DESCRIPTION OF THE PREFERRED EMBODIMENTS

Other characteristics and advantages of the invention will appear during the reading of the description of the following examples, that illustrate different preparation processes, in particular Examples 3 to 6 and 9, that show modes of implementation of the invention using boric acid.

EXAMPLE 1

This example concerns a known preparation process of a ferrierite-type zeolite. Prepare a solution A of sodium silicate (23 g of sodium silicate at 26% $SiO_2$, 8% of $Na_2O$) with 70 g of water. The solution is heated to 60° C. for 20 minutes. A solution B containing 3.15 g of aluminum sulfate [$Al_2(SO_4)_3, 14H_2O$] with 50 g of water is heated for 20 minutes at 70° C. under agitation, until a clear solution is obtained.

The solution B is added to solution A and a precipitate will form.

Add 20 g of water to this mix, under agitation, then add, drop by drop, pure sulfuric acid, until a pH of 8 is obtained.

To the resulting viscous mix, add 20 g of water and heat under agitation for 40 minutes. The resulting gel is then washed with distilled water and centrifuged. This operation is repeated 8 times.

To the gel thus prepared, add, under agitation, a mix of 0.4 g of NaOH and 0.4 g of KOH in 10 g of water, the whole being heated to 80° C. under agitation for one hour. The final weight of the gel obtained is between 54 and 55 grams.

The crystallization is performed by transferring the gel into an autoclave, which is then sealed, agitated, and heated to 180° C. for three days (rotation speed: 300 rpm).

The shaping of 22 grams of the obtained product is performed by mixing it with 5.45 g of Pural Alumine SB and 31 ml of water. After forming of the paste, it is extruded through a 1.8 mm diameter drawplate. The extrudes thus obtained are dried in 120° C. air for one night, then calcinated by air by regularly raising the temperature from the room temperature to 500° C. at the rate of 1.5° C./minute.

EXAMPLE 2

This example is derived from Example 1.

Use a solution A that contains 23 g of sodium silicate (26% $SiO_2$) and 150 g of water, then heat to 60° C. for 20 minutes. Solution B containing 3.15 g of $Al_2(SO_4)_3, 14 H_2O$ with 150 g of water is heated for 20 minutes at 70° C.

The steps that follow are identical to those of Example 1.

EXAMPLE 3

This example illustrates the implementation of the process described in the invention.

A solution A is prepared, identical to that of Example 1.

A solution B containing 1.24 g of boric acid $B(OH)_3$, 2.96 g of $Al_2(SO_4)_3, 14 H_2O$ and 50 g of water is prepared under agitation at 70° C. for 20 minutes. The solution B is added to solution A under agitation. A precipitate forms. The pH is near 10.

20 g of water are added under agitation. After 20 minutes add sulfuric acid drop by drop until the pH is lowered to 8. At this point, the mix is very viscous and 20 g of water are added, while maintaining a temperature of 70° C., under agitation for 40 minutes.

The gel is then washed 8 times with distilled water (200 g each time).

To this gel, a solution C is added (0.4 g of NaOH, 0.4 g of KOH and 10 g of water) under agitation at 80° C. for one hour. The weight of the final gel ranges from 54 g to 55 g.

The crystallization is performed in an autoclave at welded pressure for three days at 180° C. under centrifugal agitation (300 rpm). Then, perform a calcination by air flow, raising the temperature from room temperature to 500° C. at the rate or 1.5° C./minute. The 500° C. temperature is maintained for 12 hours.

Then activate the ferrierite. The substitution of the Na and of the K is performed by three consecutive flux exchanges in the presence of $NH_4NO_3$ 1M (250 ml). These exchanges are followed by a rinsing with distilled water, of a drying for one night at 120° C. then by another calcination such as the one described above but maintaining the final temperature (500° C.) for only 4 hours.

The shaping is performed as in Example 1.

EXAMPLE 4

Proceed as in Example 3, but before the crystallization in autoclave, the gel is aged for 2 days at 25° C.

The crystallization, calcination and activation steps are identical to those of Example 3.

The shaping is performed as in Example 1.

EXAMPLE 5

This example is also a modification of Example 3.

Proceed as in Example 3, but before the crystallization, add 1% of weight in seeds of the Example 3 synthesized zeolite. The crystallization is performed for 2 days at 180° C. of for 1 day at 195° C.

The shaping is performed as in Example 1.

EXAMPLE 6

Proceed as in Example 3, but lower the amount of aluminum.

Prepare solution A in the same manner as in Example 3.

Prepare a solution B containing 2.45 g of $Al_2(SO_4)_3$, $14H_2O$ and of 1.24 g of $B(OH)_3$, in 50 g of water. Solution B is heated to 70° C. under agitation for 20 minutes.

The following steps are identical to those described in Example 3.

EXAMPLE 7

The ferrierite of this example is prepared using, by the usual method, of a structuring agent: 10.87 g of pyrrolidine are added to 48.4 g of silica-sol (type AS40, 40% $SiO_2$) under agitation at room temperature. After 15 minutes of agitation, a homogeneous solution A is obtained. A solution B, consisting of 5.0 g of NaOH, 3 g of $NaAlO_2$ and 136 g of water, is prepared at 70° C., under agitation for 40 minutes, to obtain a clear solution.

Solution B is then added to solution A under agitation, to obtain a homogenous gel that is agitated for 1 hour.

This gel is transferred to an autoclave that is closed and heated to 180° C. for 22 days.

The shaping is performed as in Example 1.

EXAMPLE 8

This example also includes the use of a structuring agent in the preparation.

29 g of Na (26% $SiO_2$) silicate are dissolved in 70 g of water, the solution A being heated under agitation at 60° C. for 20 minutes.

A solution B (2.97 g of $Al_2(SO_4)_3$, $14H_2O$+50 g of water) is heated to 70° C. for 20 minutes.

Solution B is added to solution A under agitation. A precipitate forms. Add 20 g of water to the resulting gel, under agitation, then add sulfuric acid drop by drop until the pH is lowered to 8.

20 g of water are added under agitation for 40 minutes at 70° C.

The gel is retrieved and washed 8 times with water.

Add 3 g of pyrrolidine to the washed gel, under agitation, then 0.47 g of NaOH (in powder form), under agitation, for one hour at room temperature.

The gel is then transferred to a sealed autoclave, heated to 180° C. under agitation for three days (rotation speed 300 rpm).

Shaping is performed as in Example 1.

EXAMPLE 9

This example illustrates an implementation that conforms to the specifications of the invention.

Prepare a solution A identical to that of Example 1.

A solution B containing 1.24 g of boric acid $B(OH)_3$, 2.96 g of $Al_2(SO_4)_3$, $14H_2O$ and 50 g of water is prepared under agitation at 70° C. for 20 minutes. Solution B is added to solution A under agitation. A precipitate forms. The pH is near 10.

20 g of water are added under agitation. After 20 minutes, add sulfuric acid drop by drop until the pH is lowered to 8. At this point, the mix is very viscous and 20 g of water are added, while maintaining the temperature at 70° C., under agitation, for 40 minutes.

The gel is then washed 8 times with distilled water (20 g each time).

To the gel a solution C ((0.4 g of NaOH, 0.4 g of KOH and 10 g of water) is added under agitation at 80° C. for 1 hour. The final weight of the gel ranges from 54 g to 55 g.

Crystallization is performed in an autoclave, at wielded pressure for 3 days at 180° C. and agitated (rotation speed 300 rpm).

Then, perform a calcination by air flow, raising the temperature from the ambient temperature to 500° C. at the rate of 1.5° C./minute. Maintain this temperature for 12 hours.

Then activate the ferrierite. The substitution of the Na and of the K is performed by three consecutive flux exchanges in the presence of $NH_4NO_3$ 1M (250 ml). These exchanges are followed by a rinsing with distilled water, of a drying for one night at 120° C. then by another calcination such as the one described above but maintaining the final temperature (500° C.) for only 4 hours.

Platinum is then laid down by the means of a solution of 110 g of permuted water and of 0.324 g of $Pt(NH_3)_4Cl_2H_2O$ put in contact with 22.4 g of ferrierite. A static contact of 16 hours in imposed before the aqueous phase is removed with a rotary evaporator followed by a drying overnight at 120° C. Finally, a calcination of the precursor formed is effected by air, raising the temperature in a linear manner from room temperature to 300° C. This temperature is maintained for one hour, then the increase is resumed until 500° C.

This catalyst is then shaped as described in Example 1.

It is to be noted that the crystallization step of this process follows the specifications of the invention, or hydrothermal synthesis, can be performed using other energy sources, particularly microwaves, which allows for the reduction of the duration of this step, while maintaining the same temperature.

All synthesized materials obtained in these examples present the crystalline structure of ferrierite and their crystallographic characteristics are brought together in the following Table 1.

TABLE I

| Example | 1 | 2 | 3 | 4 | 5 | 6 | 7 | 8 |
|---|---|---|---|---|---|---|---|---|
| Si/Ai (chemical analysis) | 9.2 | 9.1 | 10.8 | 11 | 10.7 | 9.3 | 8.8 | 8.9 |
| Si/Al(RMN) a) | 9.8 | 9.9 | 11.8 | 11.5 | 10 | 10.5 | 7 | 9 |
| Size of Crystals Measured in μm b) | 0.5 to 1 | 0.5 to 1 | 0.5 to 1 | 0.5 to 1 | 0.5 to 1 | 0.5 to 1 | 20 to 30 | 1 to 2 |

TABLE I-continued

| Example | 1 | 2 | 3 | 4 | 5 | 6 | 7 | 8 |
|---|---|---|---|---|---|---|---|---|
| Height of the RN rays 2θ = 9.4 degrees c) | 53 | 52 | 60 | 100 | 40 | 55 | 20 to 30 | 80 | a) values measures from 29Si spectrum;
b) estimated by sweeping electronic microscope (MEB) medium;
c) the height is fixed to 100 for the sample that crystallized best.

If we admit, as Szostak R. contends in "Molecular Sieves", published by Van Nostrand Reinhhold, New York, 1898, p. 290, that the height of diffraction rays (pics) of RX is in direct relation to the degree of crystallization, for crystals with a size 0.3 μm or greater, it appears, comparing the heights of the pics to 29=9.45° C., in Table 1, that the materials from Example 1 to 8 are well crystallized (refer to the work "Collection of Simulated XRD Powder Pattern for Zeolites" by Tracy Higgins and Von Balmoos, published by Elsevier, 1996). Nevertheless, the highest level of crystallization is achieved by the material from Example 4.

Furthermore, the examination of the photos of the samples of zeolites corresponding to the diverse examples of preparation, obtained by sweeping electronic microscopes, has permitted the evaluation of the size of the crystals of these samples. This size in indicated in Table 1.

Catalytic Tests of the Ferrierites Obtained in the Isomerization of the Butene-1 in Isobutene All the samples of zeolites from Examples 1, 3 to 5, and 8, are tested in the same experimental condition:
Weight of catalyst: 0.1–0.2 g,
Temperature: 400° C.
pph (weight of butene-1/weight of catalyst/hours): 5 h−1.
Partial pressure of the butene-1:26 kPa (complement to atmospheric pressure, 101 kPa, by using $N_2$).

During the isomerization reaction, an equilibrium is reached between the linear butenes, butene-1 and butene-2 cis and trans.

The progress of the isomerization, in function of the reaction time are gathered in Table 2, to follow, in which are listed:

The isobutene yield, that is to say the ratio of the weight of isobutene obtained to the weight of initial butene-1, expressed in percentages.

The conversion of linear butenes, that is to say the ratio of the difference between the initial weight of the butene-1 and the final weight of butene-1 and butene-2, and the initial weight of butene-1, expressed in percentage.

The selectivity of isobutene, that is to say the ratio of the weight of isobutene obtained to the weight of isobutene converted, expressed in percentage.

TABLE 2

| | Example | | | | | | | | | | | | | |
|---|---|---|---|---|---|---|---|---|---|---|---|---|---|---|
| | 1 | | | | | 3 | | | | | 4 | | | |
| Reaction Time (h) | 1 | 6 | 12 | 24 | 36 | 1 | 6 | 12 | 24 | 36 | 1 | 6 | 12 | 24 | 16 |
| Isobutene Yield (%) | 16,5 | 24 | 31,5 | 34,5 | 23 | 23 | 30,8 | 37 | 40 | 40 | 29 | 38,5 | 40 | 40 | 40 |
| Conversion of the n-butenes (%) | 68,5 | 60 | 43 | 40 | 25,5 | 72 | 61,5 | 49 | 46 | 44 | 58 | 45 | 43 | 43 | 42,5 |
| Selectivity of the isobutene (%) | 24 | 40 | 73 | 86 | 90 | 32 | 50 | 75,5 | 87 | 91 | 50 | 80 | 93 | 93 | 94 |

| | Example | | | | | | | | |
|---|---|---|---|---|---|---|---|---|---|
| | 5 | | | | | 8 | | | |
| Reaction Time (h) | 1 | 6 | 12 | 24 | 36 | 1 | 6 | 12 | 24 | 36 |
| Isobutene Yield (%) | 26 | 37,7 | 39 | 28,5 | 20 | 34,8 | 38 | 37,5 | 15 | — |
| Conversion of the n-butenes (%) | 56 | 49,6 | 44 | 31 | 21,7 | 58 | 47,5 | 43 | 16 | — |
| Selectivity of the isobutene (%) | 46,5 | 76 | 88 | 92 | 92 | 60 | 80 | 87 | 95 | — |

The annexed graph of table 1 shows the yield of isobutene (in percentages) as a function of the reaction time (in hours) for the examples of Table 2. Note that catalysts 3 and 4 of the invention perform best, notably in isobutene yield after 12 hours, and that they retain their efficiency well beyond 36 hours. The tests performed have also shown that the zeolites obtained without structuring agents possess a better isomerization activity than standard catalysts used in this field.

Test Performed with the Catalyst of Example 9 in the Hydrocracking and Hydroisomerization Reactions The activity of this catalyst in the hydrocracking/hydroisomerization reactions are tested on two platforms: the n-dodecane and the n-hexadecane. The conditions of the reactions are:
Temperature: 250 to 300° C.

Pressure: 20 to 50 bars=2 to 5 MPa
$H_2$/HC (charge): 3 to 6
PPH: 0.75 to 2 $h^{-1}$ 7 g of catalyst are placed in the reactor for each test.

Before any reaction, the catalyst is reduced in-situ in the reactor under a flow of 6 $1h^{-1}$ of hydrogen at 30 bars (3 MPa) and to a temperature of 500° C. for 2 hours. The charge is dried to the maximum with zeolite 4A before being mixed to the hydrogen and placed in contact with the catalyst.

1—Transformation of the n-hexadecane

As illustrate the results in Table 3 below, the transformation of the hexadecane on the catalyst of Example 9 containing 0.8% in weight of Pt in relation to the ferrierite subtract ends in the formation of materials whose nature depend closely to the operational conditions followed. Actually, this catalyst can either boost the isomerization of the charge, or its hydrocracking.

Temperature, of course, is an important element that comes into play on both the activity and the selectivity of the catalysts. Note the rise of the $n\text{-}C_{16}$ conversion with the rise in temperature, reaching 100% at 300° C. (30 bars, $H_2$/HC= 3, pph=1). This rise in the conversion by the effect of temperature triggers a rise in the hydrogenolization capacity of the catalyst at the expense of the isomerization of the elements under reaction. Furthermore, the creation of light compounds ($C_4$) is encouraged by the increase in temperature. In view of the results shown in Table 3, a temperature near 280° C. seems to be the most interesting to obtain a high conversion without encouraging too much the formation of light compounds ($C_4$).

ments produced are not, at first view, interesting for gasoline constitution, they are to constitute the base of high quality and high V.I. (viscosity index) oils that require branched long-chained paraffins.

2—Transformation of the dodecane

It is well-known that the interaction of paraffins with this kind of catalyst increases with the length of the carbon chain. We can therefore expect a change of the properties of the Example 9 catalyst (Pt/ferrierite) in the presence of dodecane.

The results obtained indicate a range of formed products that is very comparable to those obtained with the use of the hexadecane as reactive. Here too, the isomerization of the reagent is encouraged with the use of soft reaction conditions (low temperatures, long reaction time, low $H_2$/HC) but the hydrogenolization of this reagent under more severe conditions more readily yields light compounds ($C_1$–$C_4$). The yield of midrange cracking compounds ($C_5$–$C_{11}$) never makes up the majority under the our conditions of the reaction, yet represents a quite substantial quantity of the elements formed.

As an example, a few results of transformation of n-dodecane on Pt/Ferrierites are displayed in Table 4.

TABLE 3

Hydrocracking of n-C16 on Pt/ferrierites

| T(° C.) | P (bar) | $H_2$/HC | pph $h^{-2}$ | Conversion (%)[1] | Yield iC16(%)[2] | Yield C5–C11(%)[2] | Yield C12–C15(%) |
|---|---|---|---|---|---|---|---|
| 275 | 20 | 3 | 1 | 90,2 | 45,46 | 10,01 | 9,73 |
| 275 | 30 | 3 | 1 | 78,16 | 35,14 | 10,85 | 6,72 |
| 275 | 50 | 3 | 1 | 75,25 | 31,82 | 13,67 | 5,42 |
| 275 | 50 | 6 | 1 | 75,5 | 23,63 | 8,53 | 2,91 |
| 275 | 50 | 3 | 2 | 47,9 | 22,27 | 10,06 | 4,42 |
| 250 | 30 | 3 | 1 | 24,2 | 12,4 | 3,6 | 2,8 |
| 300 | 30 | 3 | 1 | 100 | 5,80 | 33,3 | 12,8 |

[1] by conversion we mean the ratio of the difference between the initial weight of the charge and the final weight, and the initial weight of the charge. Expressed in percentage.
[2] the yield is the ratio of the weight of the products obtained to the initial weight of the product. Expressed in percentage.

The two italic lines correspond to the most favorable operating conditions, respectively, for the isomerization of the charge or for the hydrogenolization of materials containing more than 5 carbon atoms.

It was noticed that the I-paraffine/n-paraffine ratio of the different hydrocarbon families rise in a significant manner during the conversion and therefore the hydrogenolization capacity increases. This result shows that before cracking, an absorbed hydrocarbon is submitted to at least one period of isomerization.

This result is interesting for the products entering the production of gasolines ($C_5$–$C_{11}$) since the octane indicator rises with the degree of paraffin ramifications. If the ele-

TABLE 4

Hydrocracking of n-$C_{12}$ on 0.8% in weight of Pt/Ferrierite

| T(° C.) | P(bar) | $H_2$/HC | pph $h^{-1}$ | Conversion (%) | Yield iC12(%) | Yield Gasoline (%) |
|---|---|---|---|---|---|---|
| 300 | 30 | 3 | 1 | 79, 04 | 15, 14 | 35, 96 |
| 300 | 50 | 3 | 1 | 85, 21 | 14, 98 | 38, 01 |
| 300 | 50 | 6 | 1 | 79, 95 | 11, 01 | 31, 40 |
| 280 | 50 | 6 | 0, 75 | 77, 48 | 20, 01 | 39, 49 |
| 280 | 20 | 6 | 1 | 70, 26 | 24, 94 | 42, 92 |
| 280 | 30 | 6 | 1 | 69, 55 | 25, 64 | 41, 20 |
| 280 | 50 | 6 | 1 | 68, 11 | 19, 78 | 36, 39 |

Thus, the results obtained in the reaction of hydrocracking and hydroisomerization of dodecane and of hecadecane on the Pt/Ferrierite catalyst show that the use of "soft" reaction conditions (temperature<280° C., $H_2/HC \leq 3$, $pph \geq 1$) increases the isomerization of the studied reagents to the expense of their hydrogenolization. Under these conditions, the formation of products that can be used to form the base of a high quality oil (branched paraffins) is increased (45% yield).

But when the reaction temperature increases and/or the value of the $H_2/HC$ ratio decreases, or even as the pph value decreases, the yield of elements lighter than the reagents is highly increased, to become predominant. If the quantity of $C_1$–$C_4$ formed is great during the transformation of the dodecane and of the hexadecane, the yield in gasolines ($C_5$–$C_{11}$) and diesels ($C_{12}$–$C_{15}$) are interesting (around 45% under the best testing conditions).

What is claimed is:

1. Process of preparation of a ferrierite-type zeolite, with high crystallinity rate, and having an anhydrous-stage composition expressed by the formula $M_x(AlO_2)_x(SiO_2)_y$, M being a cation of at least one alkali metal and the ratio y/x is between 8 and 12, said process comprising:

obtaining a gel by adding boric acid to an aqueous solution of aluminum sulfate, and mixing with an aqueous solution containing Na and/or K and Si oxides, without the use of structuring agent; and subjecting said gel to crystallization.

2. Process according to claim 1, wherein the mixing of the solution is performed under agitation, with acidification reaching pH 8.

3. Process according to claim 2, wherein the obtained gel is washed with distilled water.

4. Process according to claim 3, wherein a solution containing alkaline metal hydroxides is added under agitation to the solution being mixed.

5. Process according to claim 4, wherein the obtained gel undergoes aging, followed by said crystallization in an autoclave, under agitation, and heating for several hours.

6. Process according to claim 5, wherein the crystallized product is washed with water and heat-dried.

7. Process according to claim 1, wherein the adding and mixing steps occur at a temperature ranging from 40° C. to 90° C.

8. Process according to claim 1, wherein the aging of the gel is performed at a temperature ranging from 25° C. to 80° C. and for a duration between 6 and 72 hours.

9. Process according to claim 1, wherein the crystallization is performed under wielded pressure, at a temperature ranging from 150° C. to 200° C., and for a period between 2 to 72 hours.

10. Process according to claim 1, wherein the crystallization is followed by calcination, then impregnation with a platinum salt solution, then evaporation, then drying, and then another calcination.

11. Process according to claim 1, wherein said at least one alkali metal is Na or K.

* * * * *